(12) United States Patent  
Pasula

(10) Patent No.: US 6,200,815 B1  
(45) Date of Patent: Mar. 13, 2001

(54) METHOD FOR MEASURING THE VOLUME OF LIQUID AND/OR SOLID IN A SUSPENSION

(75) Inventor: Mark J. Pasula, Palm Beach Gardens, FL (US)

(73) Assignee: Signet Diagnostic Corporation, Riviera Beach, FL (US)

(*) Notice: Subject to any disclaimer, the term of this patent is extended or adjusted under 35 U.S.C. 154(b) by 0 days.

(21) Appl. No.: 09/011,116

(22) PCT Filed: Aug. 1, 1996

(86) PCT No.: PCT/US96/12629

§ 371 Date: Jan. 30, 1998

§ 102(e) Date: Jan. 30, 1998

(87) PCT Pub. No.: WO97/05475

PCT Pub. Date: Feb. 13, 1997

Related U.S. Application Data

(60) Provisional application No. 60/001,824, filed on Aug. 1, 1995.

(51) Int. Cl.[7] .................................................. G01N 33/48
(52) U.S. Cl. .................. 436/63; 73/3; 73/53.01; 324/71.4; 422/82.02; 436/149; 436/150; 702/21; 702/29
(58) Field of Search .................. 436/63, 149; 422/82.02; 73/3, 53.01; 324/71.4, 605, 606, 613, 614, 691, 692, 693, 701, 713, 714, 720; 364/555, 413.08, 413.1; 702/21, 29

(56) References Cited

U.S. PATENT DOCUMENTS 4,021,117 * 5/1977 Ghode et al. .  
5,376,878 * 12/1994 Fisher .

* cited by examiner

Primary Examiner—Jan Ludlow  
(74) Attorney, Agent, or Firm—Cohen, Pontani, Lieberman & Pavane

(57) ABSTRACT

The present invention is a method of measuring the total volume of solids in a suspension, comprising the steps of: establishing a potential across a predetermined spatial volume; passing a portion of the suspension through the predetermined spatial volume; substantially continuously measuring the potential across the predetermined spatial volume over a first predetermined period of time; comparing the measured potential with a baseline; and calculating the total volume of solids in the suspension as a function of a total absolute deviation of the measured potential from the baseline. The baseline is preferably a dynamic baseline, and is determined with reference to the starting point of a sharp rise in the measured potential.

26 Claims, 6 Drawing Sheets

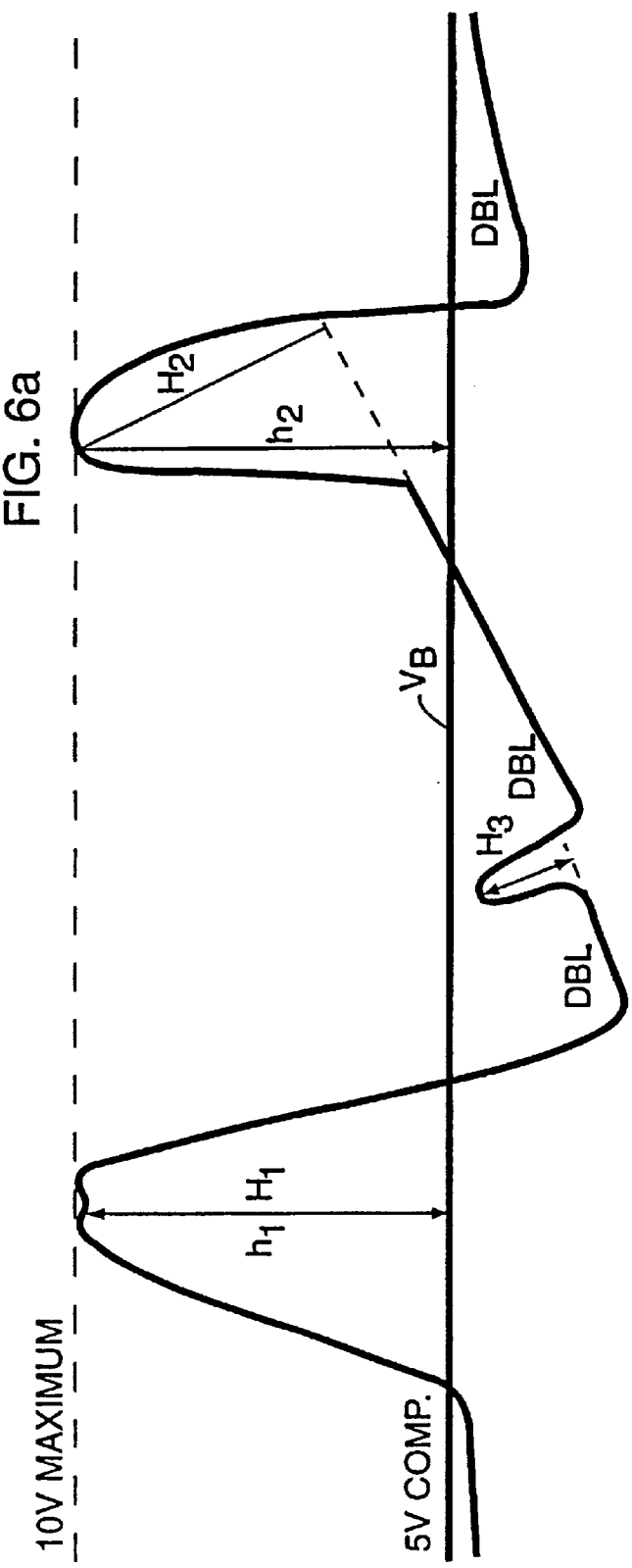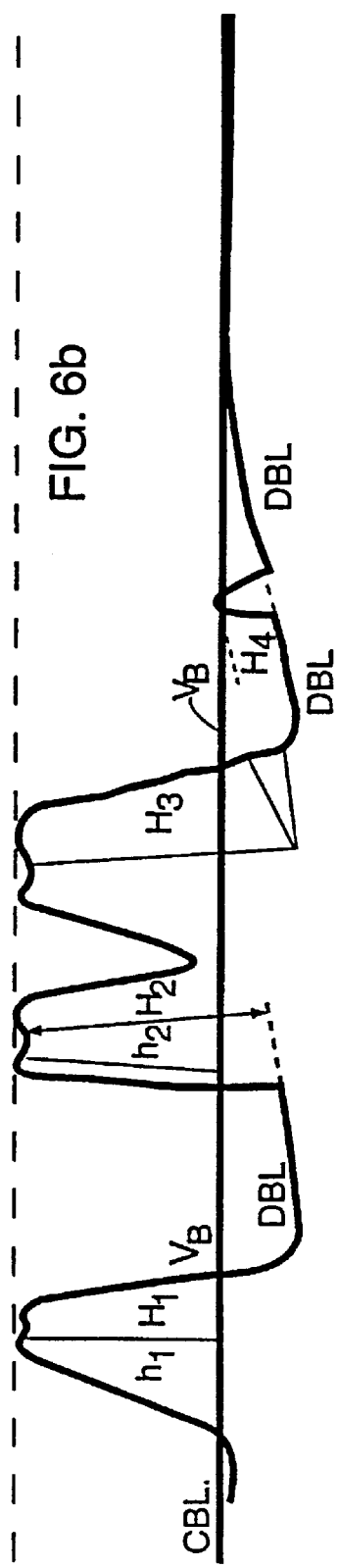

METHOD FOR MEASURING THE VOLUME OF LIQUID AND/OR SOLID IN A SUSPENSION

This application claims benefit to U.S. provisional application serial No. 60/001,824, filed Aug. 1, 1995, which is a 371 of PCT/US96/12629, filed Aug. 1, 1996.

BACKGROUND OF THE INVENTION

The present invention relates to a method for measuring the volume of solid and liquid in a suspension, such as counting the total volume of blood cells in a patient's blood or the total volume of particulate contaminants in a sample of drinking water. More specifically, the present invention relates to a method of measurement of the actual volume of liquid and/or the actual volume of solids in a liquid suspension.

In my earlier patents (U.S. Pat. Nos. 4,614,722; 4,788,155 and 5,147,785 the disclosures of which are hereby incorporated by reference), I disclosed methods for testing a subject's blood for various maladies, including allergies. The described testing of the blood permits the diagnosis of the maladies by preparing two samples of the subject's blood.

The first sample is a control sample, and the second is a test sample. A test substance having a predetermined relationship with the malady under consideration is placed into the test sample, and the blood and the substance are given the opportunity to react. The blood cells in the two samples are counted and compared, both as to number and size-distribution. If a significant difference is observed between the blood cells present in the two samples, then it may be concluded that the subject has the malady for which he was tested.

In the performance of my patented tests, I have needed to use various apparatus for counting and sizing particles, and been disappointed in inaccuracies that I have found. I have attributed the inaccuracies, in part, to the fact that my prior testing would not recognize small, subtle, changes in the size of a patient's blood cells. I therefore saw the need to develop a more accurate and reliable method of performing three-dimensional volumetric measurement of blood cells in a patient's blood. After working on such an apparatus, I also saw that it would have general applicability in other fields for measuring particles in a suspension, such as in water plants where the measurement of particulate contaminants is of serious importance, or in paint manufacturing where consistency of product is important. In short, the inventive method could have a widespread utility in the field of volumetric measurement of particles in suspensions.

Previously, attempts to count and size particles in a fluid involved methods which included individual counts of the solid particles which were triggered by deviations from a constant baseline voltage. Once the voltage deviated from the baseline, a second measurement would be taken at a predetermined interval which was intended to represent the maximum voltage, indicative of the size of the particle.

This method is faulty for a few reasons.

First, even though the rate of travel of the fluid through the aperture is known, there is no guarantee that the predetermined interval is correct. If the particle enters at an angle, for example, the measurement may be off.

Second, measurement of the initial peak of the deviation as the correct volume of the particle may not be accurate, since some particles (depending upon their angle of entry into the aperture) might have an initial deviation which is far greater than the deviation which indicates their actual volume.

Third, where the actual baseline potential differs from the presumed static baseline potential, inaccuracies develop in measuring the particle's volume, since the measurement of the volume of the particle is derived from the comparison of the deviation of the potential from an incorrect baseline starting point.

Fourth, by limiting counting to only those particles which cause a potential deviation greater than a predetermined threshold, you lose the count of actual particles which are too small to cause deviations greater than the threshold.

It was my desire, therefore, to develop a new procedure for performing the volumetric measurement of solids in a suspension, of any kind, in many different types of fluids, more accurately than heretofore known.

OBJECTS AND SUMMARY OF THE INVENTION

Accordingly, it is an object of the invention to provide a method for the volumetric measurement of particles.

It is a further object of the invention to provide a method for the volumetric measurement of particles which provides more accurate measurement of particles, especially smaller particles, than in those devices heretofore known.

It is a further object of the invention to provide a method for the volumetric measurement of the total volume of solids present in a suspension, the total volume of liquid in the suspension, and the ratio of solids to liquids in the suspension.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 3b shows the voltage readings across the aperture over the path of travel of each of the three particles shown in FIG. 3a.

FIG. 6a is a curve showing examples of readings for three particles passing through an aperture, with an illustration of the dynamic baseline being calculated..

FIG. 6b is a further curve showing exemplary readings of three different particles passing through the aperture, with an illustration of the dynamic baseline being calculated..

DETAILED DESCRIPTION OF THE PREFERRED EMBODIMENT

Figure 1:
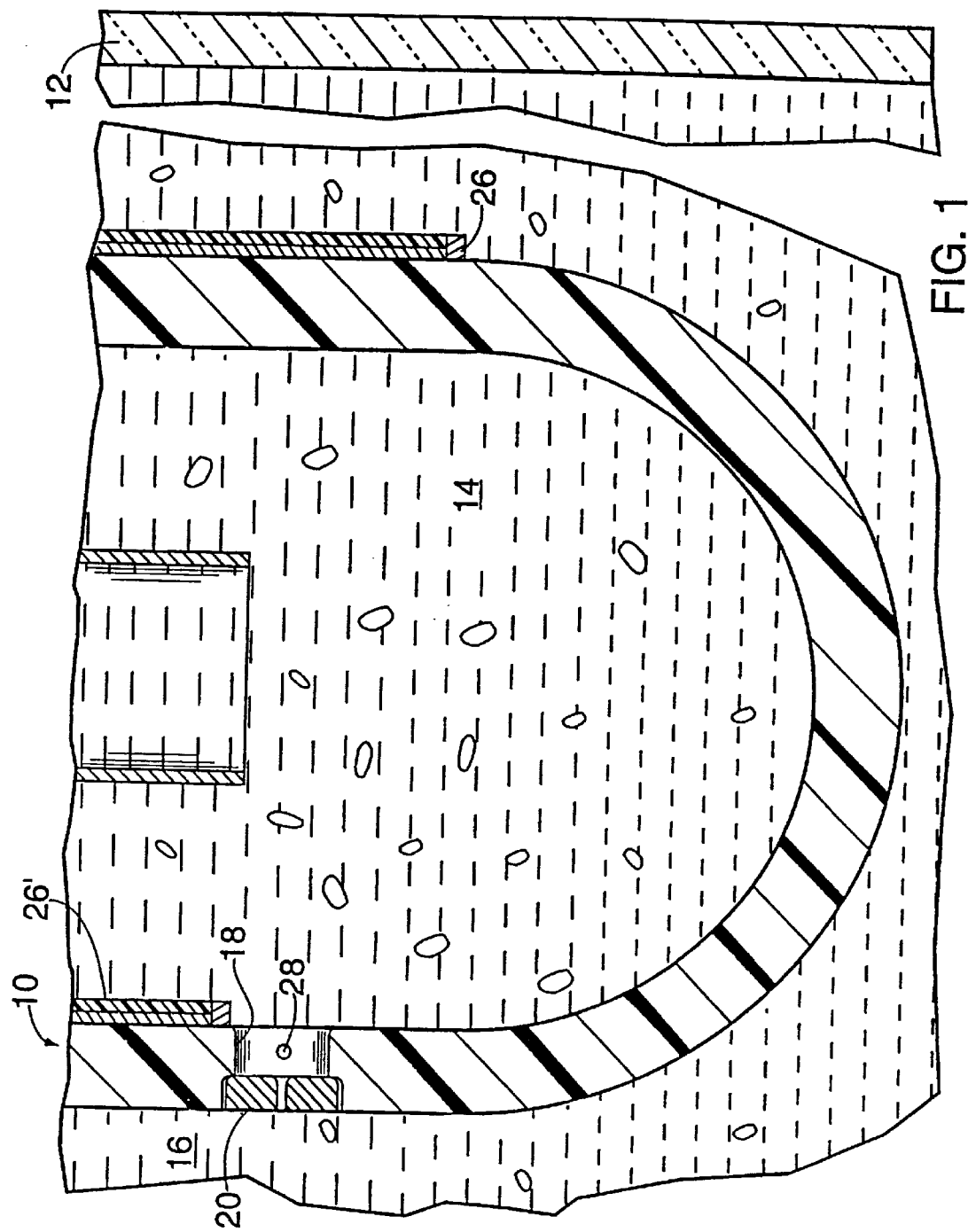
FIG. 1 is a detailed cross-section of a lower portion of an aperture tube used in the inventive method.
Figure 2:
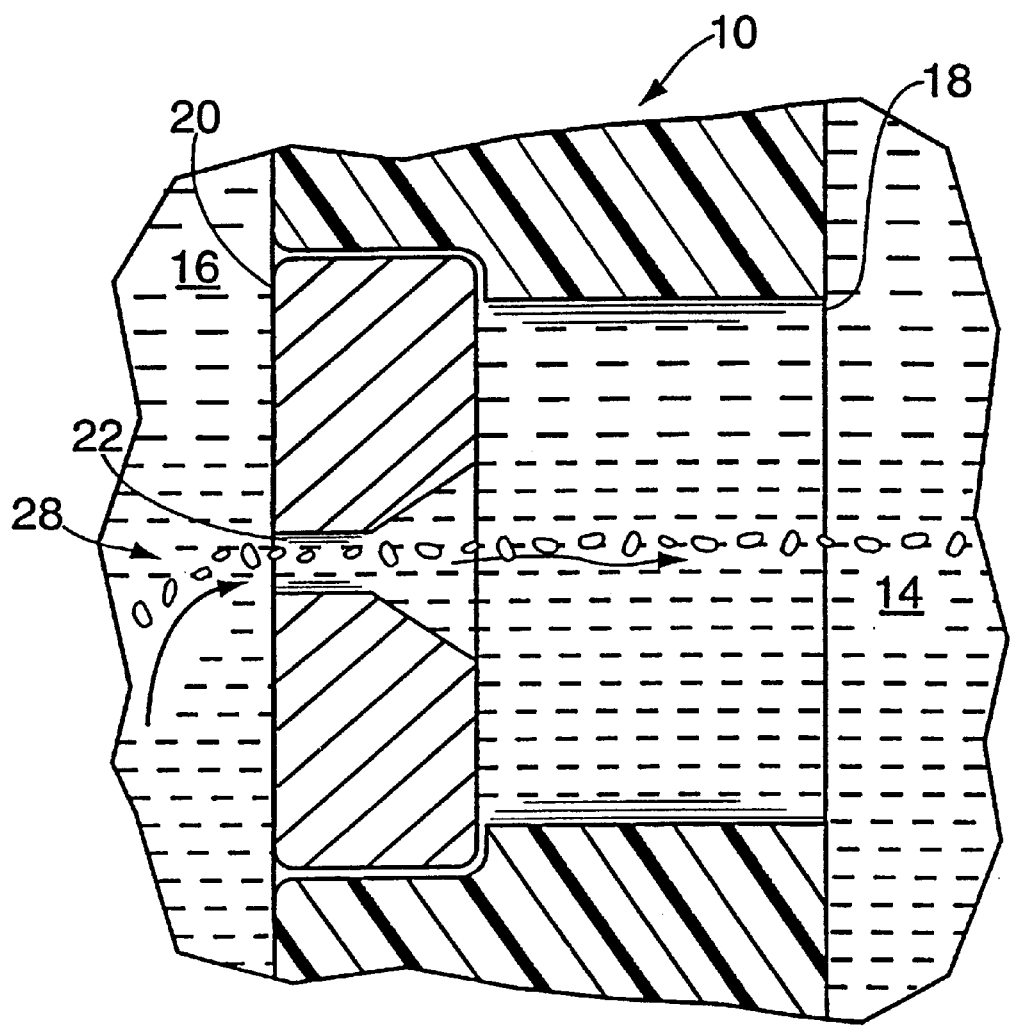
FIG. 2 is a further detail of the lower portion of the aperture tube shown in FIG. 1.

Referring now to FIG. 1, there is shown, generally at 10, the lower portion of an aperture tube 10, suspended in a fluid receptacle 12. An electrolyte 14 is shown within aperture tube 10, and a liquid suspension 16 is shown on the exterior of aperture tube 10. Aperture tube 10 is not completely solid. It has a small aperture 18 therein which provides communication between the interior and exterior of aperture tube 10. A jewel 20 having an aperture 22 is disposed in the mouth of aperture 18 on the exterior side of aperture tube 10. Aperture 18 provides the sole means of communication between the interior and exterior of aperture tube 10.

In the preferred embodiment, aperture tube 10 has walls which are approximately 1 mm thick, and, at its lowest end, has an exterior diameter of approximately 10 mm. Thus, aperture 18 has a length of approximately 1 mm. Aperture 18 also has a diameter of approximately 2 mm. Jewel 20 has an exterior diameter at least as great as the interior diameter of aperture 18, so that it completely fills aperture 18, and a thickness of approximately 200–300 microns. Aperture 22 of jewel 20 is shaped generally as a funnel, with a generally cylindrical portion having a varying diameter from 15–500 microns, depending upon the application. The cylindrical portion is positioned centrally in jewel 20 on the side thereof which is on the exterior of aperture tube 10, and extends approximately half-way through jewel 20. The remainder of aperture 22 widens at an angle of approximately 45°. The specific size and shape of the aperture jewels 20 will vary according to the application.

As will be described in detail below, particles will travel the length of aperture 18 for measurement, but the suspension will also flow therethrough. Accordingly, a buildup of vacuum (i.e. negative pressure) on the interior of aperture tube 10 (caused in known fashion) will force fluid suspension 16 to enter aperture 18 and flow into aperture tube 10. However, aperture 18 is not shown to scale in FIG. 1. In fact, the size of aperture 18 depends upon the diameter thereof, and the diameter/depth ratio may vary from 1:1 up to 1:2. The depth of aperture 18 is on the order of 100–140 microns, and its diameter is 100 microns. The diameter thereof is much larger than the diameter of a particle to be counted.

A pair of electrodes 26 and 26' are used to take the measurements in accordance with the instant method. A first electrode 26 comprises a single strand of wire, preferably platinum wire, which winds about the bottom of aperture tube. An exposed end thereof is located on the side of aperture tube 10 removed from aperture 18. It should be evident that, in order to establish an electrical connection between the two electrodes, it is necessary that they both be submerged beneath the level of the conductive suspension. This establishes the means for providing an electrical connection with the interior of aperture tube 12, as will be described presently.

The other electrode 26' is suspended within aperture tube 12, at a position removed from aperture 18. This renders it less likely that electrode 26' will be disturbed by any turbulence near aperture 18. FIG. 1 is not drawn to scale to show the general placement of electrode 26'.

One of electrodes 26 and 26' is attached to a voltage generating means (not shown) and the other to a voltage detecting means (also not shown). Which of pair of electrodes 26 and 26' generates the voltage, and which measures it, is not relevant. It is noted that, in the preferred embodiment, the two electrodes will alternate as anode and cathode, so that the electrons which flow therebetween will flow in alternating directions between measurements. This prevents the build-up of contaminants which would tend to accrete if only one electrode served as the cathode. The electrical potential across the spatial volume occupied by aperture 90 is identified as V. It will be appreciated that, while the discussion of the preferred embodiment is directed to the measuring of a voltage across aperture 18, it would be possible to perform the equivalent measurement by taking the reading of the current which passes through aperture 18. These would be equivalent readings.

It should be appreciated that measuring the volume of a particle by means of a change in the potential measured across the aperture mandates that one variable in Ohm's Law (V=IR) be constant. Thus, since the size of the particle may be measured by its resistance (R), one of the voltage (V) and current (I) must be constant. In some application, e.g. where the voltage may fluctuate due to temperature variations, constant voltage should be preferred, while in others, a constant current, and changing voltage would be preferred. Either may be done, as they are essentially the same measurement in accordance with Ohm's Law. The choice of measuring current or voltage is simple, and may be done by one of ordinary skill, depending upon the application without undue experimentation.

Similarly, the precise relationship of measured voltage and particle size will depend upon the type of particle being measured. Blood cells differ in conductivity from metallic paint particles, for example. The device used to perform the test should be calibrated before use, in known fashion, to ensure that the voltage or current being measured falls within the range of tolerances of the device, and that the precise relationship of the particle volume to potential deviation is known.

For ease of description, however, the following description shall be directed to the measurement of voltage, or potential, but it will be understood that the measurement could as easily be made of current perturbations, as described.

Figure 4:
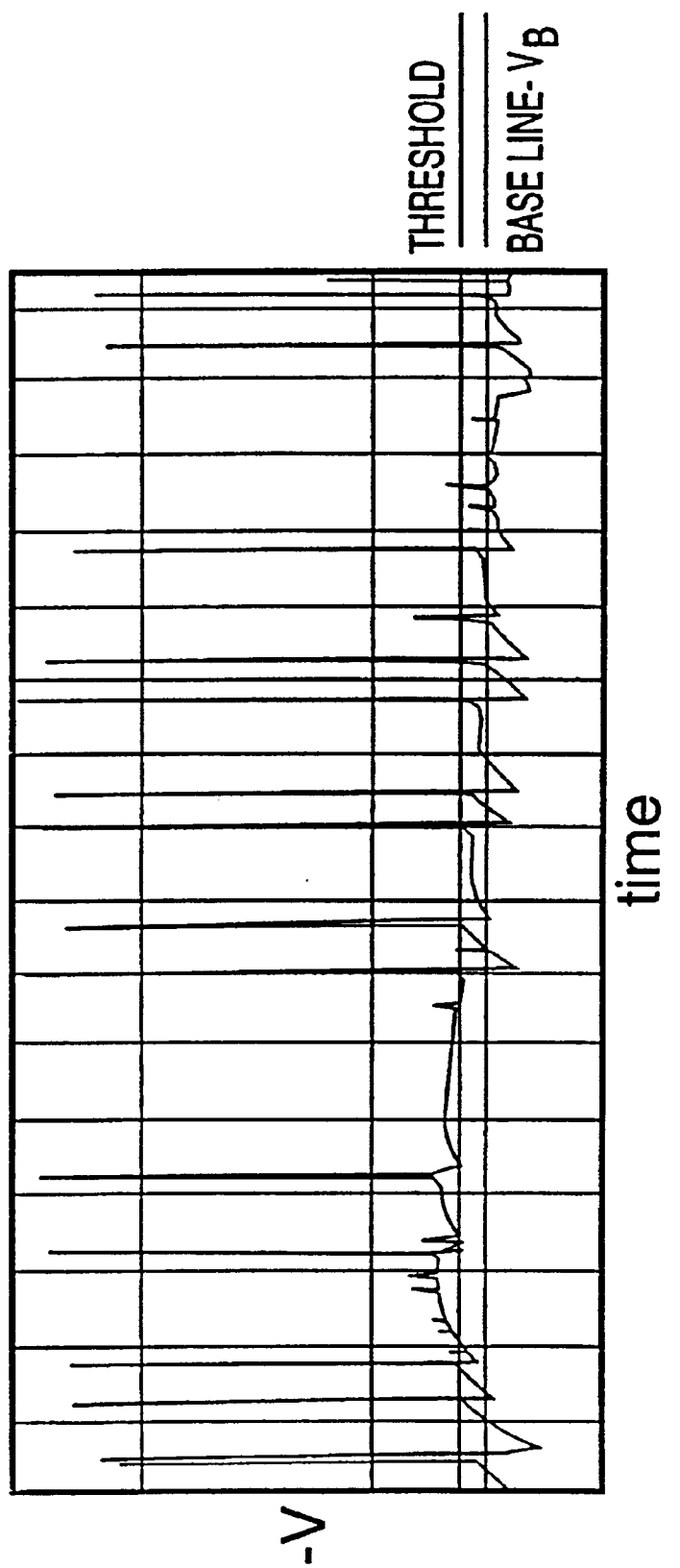
FIG. 4 is a curve showing the range of actual measurements taken over time, of a plurality of particles traveling through an aperture tube.

Returning to the description of the invention, when a voltage is produced by one of pair of electrodes 26, current will flow evenly through electrolyte 14 or blood suspension 16 (the blood suspension includes an electrolyte, as well), since they are both conductive. However, since aperture tube 12 is non-conductive, the only available conductive path between electrodes 26 and 26' is along the electrolytes found in aperture 18. When aperture 18 contains only a completely homogeneous solution of electrolytes, there is a constant voltage, of known magnitude, across aperture 18. This establishes a constant baseline voltage (see $V_B$ in FIGS. 4, 6a and 6b) which may be used as a comparative reference voltage. When a particle 28 (not shown to scale) enters aperture 18, it perturbs the voltage, and dampens V. Voltage V is monitored to ascertain the level of V prior to the commencement of any measurements, to remember that level, i.e. $V_B$.

Figure 3A:
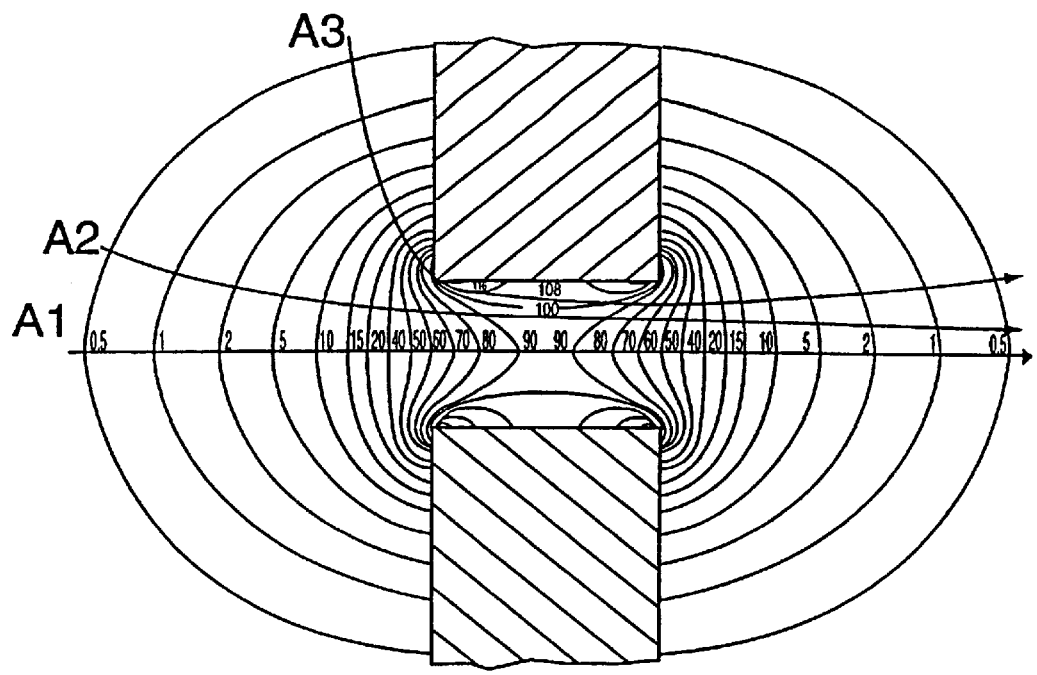
FIG. 3a shows a stylized aperture tube (with certain details omitted for clarity), showing the paths of travel of three particles therethrough.
Figure 3B:
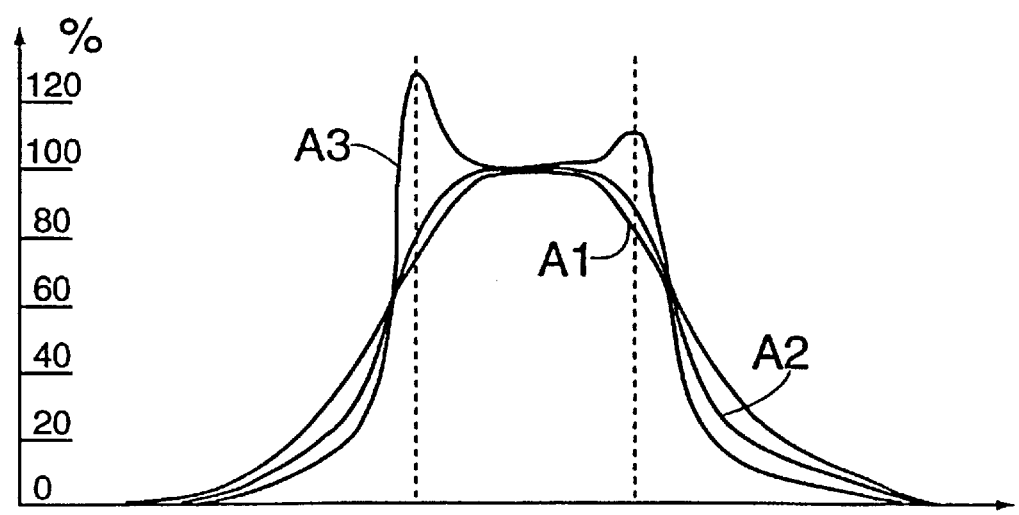

FIGS. 3a and 3b show a graphic description of a particle passing through aperture 18. The cross-section of aperture tube 10 shows three identical particles, A1–A3 going from the outside of the tube (left) to the inside (right). As they pass through aperture 18, they produce a deviation in the electromagnetic potential across aperture 18, since they interfere with the flow of the current therethrough.

Particle A1 goes through the center of the tube and will deliver a smooth signal, with its peak (the smooth plateau in the middle) representing the actual volume of that particle. Particle A2 approaches off-center (slight angle). Its signal is somewhat bigger, but this particle is also easy to measure by the peak method, since, once it reaches its peak, the potential remains generally flat until particle A2 leaves aperture 18.

Particle A3, however, is different. It approaches aperture 18 from the side at a very harsh angle and it produces a very large deviation in the potential across aperture 18 as it begins to enter aperture 18, and then decreases to its actual and accurate level.

This same particle, as it exits aperture 18, increases its signal briefly before it decreases to the plateau, which represents the actual volume of the particle. This is, effectively, the same image as when two particles are present in the aperture simultaneously. If the potential were only measured once, at the highest peak, then there will be an incorrect measurement of the particle, since its early (high) reading is so much larger than the level indicative of its actual volume.

Because the method of the instant invention measures the particle so many times, the full range of change of the reading is observed, and the correct volumetric measurement is recorded.

In the inventive method, the electromagnetic potential across aperture 18 is measured on a substantially constant basis, either as an analog signal, or as a series of many discrete but closely spaced measurements (for example, on the order of at least a million per second of real time).

Through the series of measurements, or the continuous measurement, of each particle as it passes through aperture 18, there is a complete record of the change in voltage as the particle traverses the length of the aperture. This complete record permits the generation of a graphical display of the potential deviations generated by each particle at every point of its travel through aperture 18, which is similar to an oscilloscope reading. Depending upon the precision needed, the method described herein may be used to count each particle from as few as two times, to as many as 60 times, or more, during its traverse of aperture 18. It is possible to increase the number of independent measurements to a nearly infinite number, resulting in a substantially analog measurement, depending upon the sophistication of the equipment used.

The important issue is to register the true potential perturbations when the particle passes through aperture 18, and determine the actual maximum potential perturbation, discarding false maxima. The inventive method may be used to determine the true volume of the particle.

In prior art devices, there has been a concern about "noise", i.e. the need to insure that only true particles are counted. In the prior art, this is accomplished by setting a "threshold" (see FIGS. 4 and 5). No particles registering a potential change of lower than the threshold are measured, thereby ensuring that only particles above a certain size are counted. The assumption is that any reading of lower than the threshold is not a true reading, but merely background disturbances, and are therefore not included in the actual count. This is not necessarily true.

In an ideal system, the resistivity of the fluid containing the particles is known, and perfectly constant. In such a system, the threshold, if set just above the level of the baseline voltage of the potential across the aperture would deviate only when a particle passes therethrough. In the real world, however, no system is that perfect. Real fluids which may be measured in the inventive method will not be perfectly homogeneous in the micro-environment. A fluid, such as water, may have dissolved in it a substance, such as salt, which would affect the resistivity of the sample being drawn through the aperture over time.

That change in resistivity of the fluid, although subtle, results in a change in the baseline potential measured across the aperture, without the presence of a particle in the aperture. This causes a changing true baseline level.

There may be other changes in measured potential without the presence of a particle in the aperture: electrical interference generated by nearby equipment, or the measurement apparatus itself, turbulence in the liquid or interference caused by a particle which passes, but does not enter, the aperture. Prior art devices attempted to ameliorate the effects of the disturbances by setting the threshold high enough to avoid counting most non-particulate disturbances.

However, this could also cause the device to miss small particles which cause small disturbances in the measured potential, as will be seen.

If you observe a standard oscilloscope reading of the potential measurement over time when the suspension is being tested, you will see that there appears to be a series of potential spikes caused by the passing of particles through the aperture. The baseline voltage varies due to supposed "noise" (see FIG. 4). If however, the readings are spread out, as seen in FIG. 5, the "noise" may actually not be noise at all, but may instead include information about particles passing through the aperture, and which should be measured.

Figure 5:
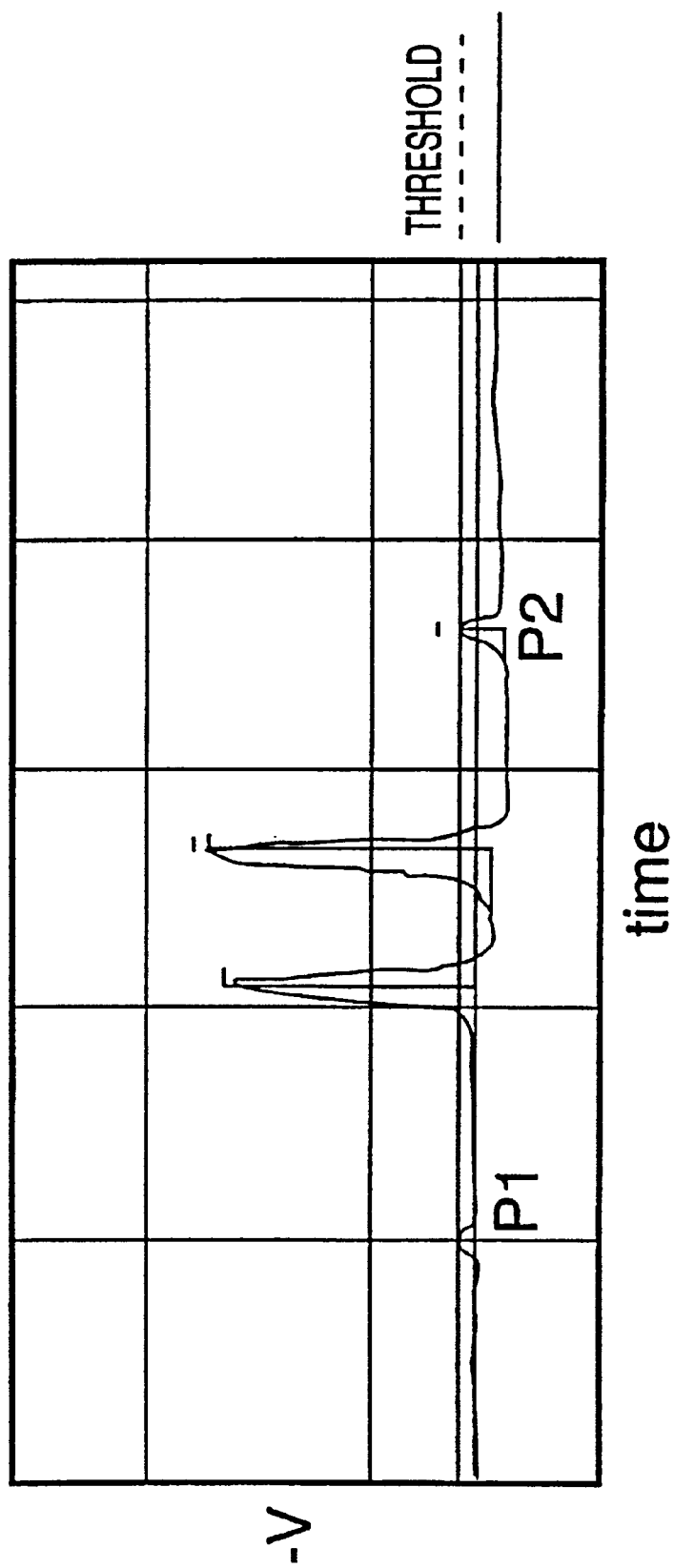
FIG. 5 is a detail of a curve such as that of FIG. 4, showing the voltage deviations caused by only four particles, two large and two small, traveling through an aperture tube, in greater detail.

Turning to FIG. 5, in fact, you will see that what was thought of as "noise" actually contains useful and important information, containing actual potential disturbances caused by particles, rather than by extraneous noise.

Using the standard threshold method (measuring dissimilar particles), small particles are often missed, see FIG. 5.

In the inventive method, therefore, I have abandoned the use of a threshold, and also abandoned the method of measuring maximum deviations from an absolute baseline. I have turned instead to a system of substantially continuous measurements of a fluid passing through the aperture tube over time, and the comparison of the maximum measured potential to a dynamic baseline potential, which is derived from the shape of the curve defined by the substantially continuous measurement of the potential across aperture 18.

The actual measurements will appear, if taken graphically, to be similar to an oscilloscope reading. This would be useful if the measurement were to be done manually, but to measure the particles automatically, we require a method which can take into account the variables of the continuous readings and analyze them to determine the true number of particles and their volumes.

We do this with two important steps.

First, we identify the correct potential deviation not by the maximum voltage perturbation, but rather at the point where it reaches the plateau, since the plateau represents the true indicator of the particle's volume. We do this by analyzing the curve described by the continuous measurement. We take a gradient, or slope, of the curve along the line of travel and, when the gradient stays constant for a predetermined period (preferably three consecutive measurement cycles) after increasing sharply (which is preferably defined as an increase in the gradient for three consecutive measurement cycles), the plateau is identified. The impulse stays substantially constant for the duration of the travel of the particle through aperture 18, and then decreases. If the shape of the recognized signal stays within the limits of the model, we recognize that as the actual measurement of the volume of the particle. In this fashion, we count only actual particles, and recognize all particles, regardless of size.

For example, referring to FIG. 6a, the particle shown as $H_1$ moves up from below what would be the constant baseline, and reaches a maximum potential and then falls. The measurement is made of the true height as the valley between two peaks, just as with particle A3 in FIG. 3b. But the true potential variation of successive particles may be masked by what happens in reality with the measurement after the particle leaves aperture 18.

As shown in FIG. 6a, the measured potential actually dips below the starting point, after the particle leaves aperture 18. If another particle ($H_3$ in FIG. 6a) enters aperture 18 before the measurement returns to $V_B$, it would have an erroneous height measurement. In fact, if it is a small particle, it may not even cause a potential deviation from its starting point of a height sufficient to reach $V_B$, and therefore would be missed by any system which relied upon a threshold in excess of $V_B$.

To overcome this, I establish a dynamic baseline which accounts for the "bounce" portion of the curve formed by the substantially continuous measurement of the potential across aperture 18. This is labeled as DBL in FIGS. 6a and 6b.

The dynamic baseline is the "starting point" of the true height measurement of the potential deviation caused by the entry of the second particle into aperture 18.

Once the curve is plotted, the relative height of $H_3$ may be determined with reference to its change from the expected DBL based upon the starting point along the curve. As shown, the height should be measured as the distance from a perpendicular to the DBL which would have a generally linear shape.

This dynamic baseline would correct a measurement such as $H_2$ in FIG. 6a, as well, because it would account for a DBL of higher than the otherwise constant baseline $V_B$.

In the event that a particle enters aperture 18 before the impulse of the prior particle ends (see particles $H_2$ and $H_3$ in FIG. 6b), it will cause an overlap of the two impulses. In this instance, the dynamic baseline for particle $H_3$ is calculated as the projected intersection of the leading edge of the perturbation of particle $H_3$ and the extended dynamic baseline of the prior particle $H_2$.

Thus, we measure the true volume of each particle which passes through aperture 18 by means of this dynamic baseline. Rather than compare the maximum potential to the constant baseline, we compare it to the value of the potential immediately prior to the increase of the impulse. As we identify and memorize the shape of the signal by the change in the impulse and by the duration of the actual perturbation, we can now identify the volume of the particle by calculating the integral of the impulse (i.e. the area under the curve formed by the continuous measurement of the potential across the aperture with respect to the dynamic baseline).

A similar calculation of the particle's volume may be obtained by monitoring the duration of the impulse. Larger particles produce longer impulses. Particles begin to cause a perturbation in the potential even before entry into aperture 18, and larger particles cause the perturbation from further away than do smaller particles. Knowing the duration also assists in determining the area under the curve, for calculating more precisely the true area of the impulse.

As a final note, once the total volume of solids is determined by the above method, the volume of liquids may be easily determined, as the difference between the total volume of solids measured by the method from the total volume of the suspension which has flowed through aperture 18 during the time period that the potential measurement is taken. The rate of flow through the aperture is known, and so the total volume is known. Once the volumes of solids and liquid are determined, the ratio may be calculated.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A method for measuring the total volume of solids in a suspension, comprising the steps of:
    establishing a potential across a predetermined spatial volume;
    passing a portion of said suspension through said predetermined spatial volume;
    substantially continuously measuring said potential across said predetermined spatial volume over a first predetermined period of time;
    comparing said measured potential with a baseline; and
    calculating the total volume of solids in said suspension as a function of a total deviation of said measured potential from said baseline.

2. The method of claim 1, wherein said substantially continuous measured potential forms a curve, and said function is an integral of said curve, so that the total volume of solid material is represented by the total area under said curve.

3. A method for measuring the total volume of solids in a suspension, comprising the steps of:
    establishing a potential across a predetermined spatial volume;
    passing a portion of said suspension through said predetermined spatial volume;
    substantially continuously measuring said potential across said predetermined spatial volume over a first predetermined period of time;
    comparing said measured potential with a baseline; and
    calculating the total volume of solids in said suspension as a function of a total deviation of said measured potential from said baseline;
    wherein said substantially continuous measured potential forms a curve, and said function includes determining a gradient of said curve.

4. The method of claim 3, wherein said function further includes identifying the presence of a particle in the predetermined spatial volume by comparing changes in said gradient over time.

5. The method of claim 4, wherein the presence of a particle in said predetermined spatial volume is identified when said comparison of changes in said gradient shows that said gradient has remained substantially constant for a second predetermined period of time.

6. The method of claim 5, wherein said substantially continuous measurement of said potential comprises a series of discrete measurements.

7. The method of claim 6, wherein said series of discrete measurements comprises at least one million measurements per second.

8. The method of claim 7, wherein said second period of time is no fewer than three of said discrete measurements.

9. The method of claim 5, wherein the presence of a particle to be measured is indicated by a sharp increase in said gradient.

10. The method of claim 9, wherein baseline is a dynamic baseline located at the value of said potential at a point on said curve immediately prior to said sharp increase in said gradient, and said volume of said particle is measured from said dynamic baseline.

11. The method of claim 10, further comprising the step of storing said volume of each said particle.

12. The method of claim 11, further comprising the step of summing the volume of all measured particles, thereby measuring the total volume of all solid particles in said suspension.

13. A method for measuring the total volume of solids in a suspension, comprising the steps of:
- establishing a potential across a predetermined spatial volume;
- passing a portion of said suspension through said predetermined spatial volume;
- substantially continuously measuring said potential across said predetermined spatial volume over a first predetermined period of time;
- comparing said measured potential with a dynamic baseline; and
- calculating the total volume of solids in said suspension as a function of a total deviation of said measured potential from said dynamic baseline.

14. The method of claim 13, wherein said substantially continuous measured potential forms a curve, and said function is an integral of said curve, so that the total volume of solid material is represented by the total area under said curve.

15. The method of claim 13, wherein said deviation from said dynamic baseline is measured from a perpendicular measurement of the height of the maximum potential perturbation from said dynamic baseline.

16. The method of claim 13, further comprising measuring the duration of each perturbation of said potential with respect to said dynamic baseline to determine said area under said curve.

17. A method for measuring the total volume of solids in a suspension, comprising the steps of:
- establishing a potential across a predetermined spatial volume;
- passing a portion of said suspension through said predetermined spatial volume;
- substantially continuously measuring said potential across said predetermined spatial volume over a first predetermined period of time;
- comparing said measured potential with a dynamic baseline; and
- calculating the total volume of solids in said suspension as a function of a total deviation of said measured potential from said dynamic baseline;
- wherein said substantially continuous measured potential forms a curve, and said function includes determining a gradient of said curve.

18. The method of claim 17, wherein said function further includes identifying the presence of a particle in the predetermined spatial volume by comparing changes in said gradient over time.

19. The method of claim 18, wherein the presence of a particle in said predetermined spatial volume is identified when said comparison of changes in said gradient shows that said gradient has remained substantially constant for a second predetermined period of time.

20. The method of claim 19, wherein said substantially continuous measurement of said potential comprises a series of discrete measurements.

21. The method of claim 20, wherein said series of discrete measurements comprises at least one million measurements per second.

22. The method of claim 21, wherein said second period of time is no fewer than three of said discrete measurements.

23. The method of claim 19, wherein the presence of a particle to be measured is indicated by a sharp increase in said gradient.

24. The method of claim 23, wherein dynamic baseline is located at the value of said potential at a point on said curve immediately prior to said sharp increase in said gradient, and said volume of said particle is measured from said dynamic baseline.

25. The method of claim 24, further comprising the step of storing said volume of each said particle.

26. The method of claim 25, further comprising the step of summing the volume of all measured particles, thereby measuring the total volume of all solid particles in said suspension.

* * * * *